(12) United States Patent
Ham et al.

(10) Patent No.: US 11,458,087 B2
(45) Date of Patent: Oct. 4, 2022

(54) **METHOD OF ISOLATING CANNABIDIOL FROM *CANNABIS* PLANT AND USE THEREOF**

(71) Applicant: KOREA INSTITUTE OF SCIENCE AND TECHNOLOGY, Seoul (KR)

(72) Inventors: Jungyeob Ham, Gangneung-si (KR); Taejung Kim, Gangneung-si (KR); Sungdo Ha, Gangneung-si (KR); Bong Chui Chung, Seoul (KR); Seok Lee, Seoul (KR); Pilju Choi, Gangneung-si (KR); Bong Geun Song, Gangneung-si (KR); Deok Ha Woo, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/893,099

(22) Filed: Jun. 4, 2020

(65) Prior Publication Data
US 2020/0383893 A1 Dec. 10, 2020

(30) Foreign Application Priority Data

Jun. 5, 2019 (KR) ........................ 10-2019-0066879

(51) Int. Cl.
| | | |
|---|---|---|
| *A61K 36/00* | (2006.01) | |
| *A61K 8/49* | (2006.01) | |
| *A61K 31/352* | (2006.01) | |
| *A61K 36/73* | (2006.01) | |
| *A61K 31/05* | (2006.01) | |

(52) U.S. Cl.
CPC .............. *A61K 8/498* (2013.01); *A61K 31/05* (2013.01); *A61K 31/352* (2013.01); *A61K 36/73* (2013.01); *A61K 2236/35* (2013.01)

(58) Field of Classification Search
CPC ..................................................... A61K 36/00
USPC ......................................................... 424/725
See application file for complete search history.

(56) References Cited

FOREIGN PATENT DOCUMENTS

WO   WO 2018/000094 A1   1/2018

OTHER PUBLICATIONS

Chang et al., "Microwave-Assisted Extraction of Cannabinoids in Hemp Nut Using Response Surface Methodology: Optimization and Comparative Study," Molecules (2017), vol. 22, No. 11, 1894, pp. 1-15.
Andre et al., "Cannabis sativa: The Plant of the Thousand and One Molecules", Frontiers in Plant Science, Feb. 2016, vol. 7, Article 19, pp. 1-17.
Burstein, "Cannabidiol (CBD) and its analogs: a review of their effects on inflammation", Bioorganic & Medicinal Chemistry, 2015, vol. 23, pp. 1377-1385.
Devane et al., "Isolation and Structure of a Brain Constituent That Binds to the Cannabinoid Receptor", Science, 1992, vol. 258, pp. 1946-1949, 6 total pages.
Englund et al., "Cannabis in the Arm: What Can we Learn from Intravenous Cannabinoid Studies?", Current Pharmaceutical Design, 2012, vol. 18, No. 32, pp. 4906-4914.
Hillig, "Genetic evidence for speciation in Cannabis (Cannabaceae)", Genetic Resources and Crop Evolution, vol. 52, 2005, pp. 161-180.
Philipsen et al., "Medical Marijuana: A Primer on Ethics, Evidence, and Politics", The Journal for Nurse Practitioners—JNP, 2014, vol. 10, Issue 9, pp. 633-640.
Russo et al., "Agonistic Properties of Cannabidiol at 5-HT1a Receptors", Neurochemical Research, 2005, vol. 30, No. 8, pp. 1037-1043.
Stephanie Pain, "A potted history", Nature, Sep. 24, 2015, vol. 525, S10-S11.
Office Action dated Apr. 2, 2021, in Republic of Korea Patent Application No. 10-2019-0066879.

*Primary Examiner* — Michael V Meller
(74) *Attorney, Agent, or Firm* — Birch, Stewart, Kolasch & Birch, LLP

(57) ABSTRACT

Provided are a method of preparing a *cannabis* processed product having an increased CBD content in an efficient and economic manner, through decarboxylic acid reaction by microwave irradiation of *cannabis* using various extraction solvents, and use of the processed product having an increased CBD content prepared by the method, a fraction thereof, and a single ingredient of CBD, in foods, drugs, and cosmetics.

1 Claim, 17 Drawing Sheets

METHOD OF ISOLATING CANNABIDIOL FROM *CANNABIS* PLANT AND USE THEREOF

CROSS-REFERENCE TO RELATED APPLICATION

This application claims the benefit of Korean Patent Application No. 10-2019-0066879, filed on Jun. 5, 2019, in the Korean Intellectual Property Office, the disclosure of which is incorporated herein in its entirety by reference.

BACKGROUND

1. Field

The present disclosure relates to a method of increasing a cannabidiol content (CBD) in *Cannabis sativa* L. and an extract thereof using microwave, and use thereof.

2. Description of Related Art

*Cannabis* (*Cannabis sativa* L.) is an annual plant belonging to the genus *Cannabis* in the family Cannabaceae, which has been widely cultivated in temperate and tropical areas, mainly in Central Asia for 12,000 years, and includes wild-type *cannabis*, and it collectively refers to *cannabis chemovars*, which contain different kinds of cannabinoid compounds known as medical/pharmaceutical ingredients, and variants thereof, *Cannabis sativa* subspecies *sativa* including variants var. *indica* and var. *kafiristanica*, *Cannabis sativa* subspecies *indica*, *Cannabis sativa* subspecies *ruderalis*, and also plants which are the result of genetic crosses, self-crosses, or hybrids thereof (*Genetic Resources and Crop Evolution* 2005, 52, 161, *Nature* 2015, 525, S10).

According to Korean and Chinese traditional medical records, mazain (麻子仁) or hwamain (火麻仁), which is a peeled seed of *cannabis*, has been used for constipation, diabetes, pain diseases, menstrual disorders, skin diseases, dysentery, etc., and *cannabis* weed which is a *cannabis* leaf has been used for anthelmintic, hair protection, asthma, analgesic, anesthetic, diuretic purposes, etc. Further, *cannabis* root has been used to treat difficult deliveries and to relieve blood stasis, *cannabis* skin has been used for bruises, and irritant rash and distending pain, *cannabis* flower has been used for paralysis, itching, etc., and *cannabis* flower neck has been used for difficult deliveries, constipation, gout, insanity, insomnia, etc. There are records that all parts of *cannabis* are appropriately used according to diseases.

*Cannabis* includes about 400 compounds, and most of them are cannabinoids, terpenes, and phenolic compounds. There are about 90 kinds of cannabinoids, which are medically/pharmacologically important natural ingredients, and there are many ingredients found only in *cannabis* (*Frontiers in Plant Science* 2016, 7, 19).

Among the ingredients of *cannabis*, substances known as psychotropic cannabinoids are $\Delta^9$-tetrahydrocannabinol ($\Delta^9$-THC), cannabinol (CBN), cannabinodiol (CBDL), and cannabidiol (CBD), which is a non-psychotropic ingredient, is known to exhibit physiologically active effects through various receptors in the human body, including adrenergic receptors and cannabinoid receptors.

In particular, while scientists were studying the mechanism of psychotropic action of *cannabis*, they discovered in 1988 a receptor in the brain, to which cannabinoid selectively binds, indicating that molecules similar to cannabinoid are also produced in our body. These cannabinoid molecules are fatty acid-type neurotransmitters locally produced in the brain, and also called anandamide (Science, 1992, 258, 1946). *Cannabis* receptors currently known are divided into two kinds; CB1 receptors are distributed throughout the brain, such as the cerebral cortex, hippocampus, cerebellum, basal ganglia, etc., and CB2 receptors are mainly distributed in macrophages or peripheral tissues such as bone marrow, lungs, pancreas, smooth muscles, etc., and are closely related to the immune system.

THC, which is a main active ingredient of *cannabis* used for medicinal purposes, is an agonist with a strong affinity for CB1 receptor, and exhibits a main mechanism of psychotropic action, whereas many experimental results revealed that CBD has beneficial effects such as anti-inflammatory action, antiepileptic action, antiemetic action, anti-cancer action, etc. CBD reduces negative effects of THC (*Current Pharmaceutical Design*, 2012, 18, 4906., *Bioorganic Medicinal Chemistry*, 2015, 23, 1377), and inhibits reuptake and breakdown of anandamide which is an endogenous cannabinoid, through antagonistic action on CB1 and CB2 receptor agonists such as THC, and is also known as a serotonin receptor agonist (*Neurochemcal Research*, 2005, 30, 1037). It was also revealed that cannabichromene which is an ingredient of *cannabis* has anti-inflammatory, sedative, antifungal actions, etc., and CBN helps boost immune function by binding to CB2 receptor rather than CB1 receptor (*Frontiers in Plant Science* 2016, 7, 19), and many researches have been very actively conducted on pharmacological mechanisms of ingredients included in *cannabis*.

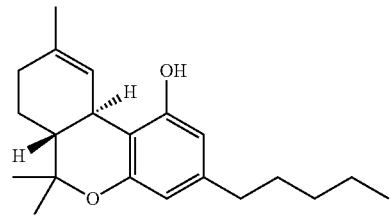

$\Delta^9$-Tetrahydrocannabinol, $\Delta^9$-THC

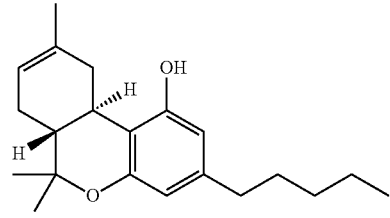

$\Delta^8$-Tetrahydrocannabinol, $\Delta^8$-THC

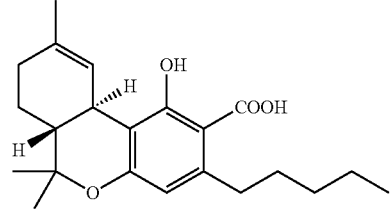

$\Delta^9$-Tetrahydrocannabinolic acid, $\Delta^9$-THCA

-continued

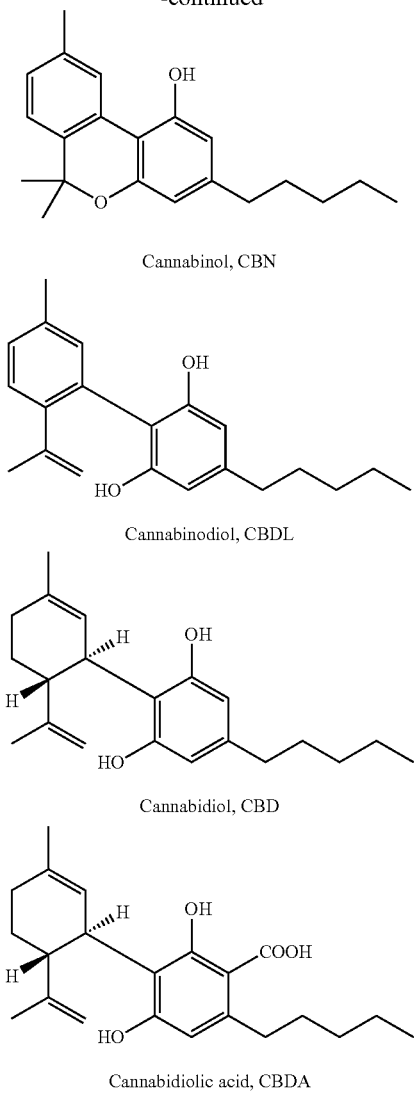

Cannabinol, CBN

Cannabinodiol, CBDL

Cannabidiol, CBD

Cannabidiolic acid, CBDA

Dronabinol (brand name: Marinol) and nabilone (brand name: Cesamet), which are THC oral forms approved by the US Food and Drug Administration (FDA), are being sold as relievers for chemotherapy-induced side-effects and as appetite stimulants for AIDS patients (*Journal of Nurse Practitioners* 2014, 10, 633), and extensive studies have been actively conducted, such as clinical trials for Epidiolex which is a liquid drug including CBD as a main ingredient for children with epilepsy, Resunab which is a CB2 receptor-binding synthetic cannabinoid formulation in the treatment of systemic lupus erythematosus, Cannador (THC:CBD=2:1) which is not a single THC or CBD drug but in the form of a *cannabis* extract in the treatment of multiple sclerosis and severe chronic pain disorders, etc.

Accordingly, the present inventors have developed technologies to increase extraction yields of the main pharmaceutical ingredients of *cannabis* and to increase a content of CBD using a microwave processing technology which has been accumulated until now, and as a result, they found that CBD is easily converted from CBDA through microwave decarboxylic acid reaction using an oil-soluble organic solvent, thereby completing the present disclosure.

SUMMARY

It is common to use ethanol in extracting cannabinoid, which is a pharmaceutical ingredient, from *cannabis*. However, since cannabinoids are fat-soluble ingredients, a high content of cannabinoids in a *cannabis* extract may be obtained by performing extraction using a low-polarity solvent.

Accordingly, the present inventors provide a method of improving an extraction yield by using aprotonic solvents rather than alcohols which are protonic polar solvents commonly used in extracting CBDA and CBD, in which an ethanol extract, a butanol extract, an ethyl acetate extract, an acetone extract, an aprotonic extract, a chloroform extract, a methylene chloride extract, and a hexane extract of *cannabis* are obtained, and then the contents of CBDA and CBD with respect to the weight of the extract of each different solvent are analyzed.

Further, the present inventors provide a preparation method of converting cannabidiolic acid (CBDA) included in *cannabis* into cannabidiol (CBD) which is a pharmaceutical ingredient by applying a natural product processing technology of deglycosylation and dehydration under microwave irradiation, in which *cannabis* or an organic solvent extract of *cannabis* is put in an airtight container, and then microwave is irradiated thereto.

Accordingly, there is provided a *cannabis* extract prepared by the above method and a processed product thereof.

Further, there is provided a CBD-containing fraction or a single ingredient of CBD from the processed product of *cannabis* prepared by the above method.

Further, there is provided a pharmaceutical composition including the *cannabis* extract, the processed product, the fraction, or the single ingredient of CBD, which is prepared by the above method.

Further, there is provided a food composition including the *cannabis* extract, the processed product, the fraction, or the single ingredient of CBD, which is prepared by the above method.

Further, there is provided a cosmetic composition for improving skin troubles, the cosmetic composition including the *cannabis* extract, the processed product, the fraction, or the single ingredient of CBD, which is prepared by the above method.

Further, there is provided a medical composition for neurological improvement, the medical composition including the *cannabis* extract, the processed product, the fraction, or the single ingredient of CBD, which is prepared by the above method.

Additional aspects will be set forth in part in the description which follows and, in part, will be apparent from the description, or may be learned by practice of the presented embodiments of the disclosure.

An aspect provides a method of isolating cannabinoid, the method including irradiating microwaves to a reaction mixture including a *Cannabis* sp. plant or an extract thereof and a solvent in an airtight container; and isolating cannabinoid from the microwave-irradiated reaction mixture.

In the method, the *Cannabis* sp. plant may include *Cannabis* sp., such as *Cannabis chemovars, Cannabis sativa, Cannabis indica, Cannabis ruderalis*, etc., wild sp. thereof, variants thereof, mutants thereof, hybrids thereof, and plants including cannabinoid, etc. Further, the *Cannabis* sp. plant may be a living plant or a dried plant. Further, the *Cannabis* sp. plant may be leaves, flower buds, fruits, trichomes, flower bracts, stems, or any part including cannabinoid. Further, the *Cannabis* sp. plant may be a dioecious plant, and its cannabinoid content may vary depending on female and male plants. The *Cannabis* sp. plant may be a female plant, a male plant, or a mixture thereof.

In the method, the extract may be obtained by a method including contacting an aprotonic solvent with the *Cannabis* sp. plant. The aprotonic solvent may be C3-C10 ester, C3-C10 ketone, or unsubstituted or halogenated C1-C6 hydrocarbon. The extract may have an increased total content of CBDA and CBD which are cannabinoids. The total content of CBDA and CBD which are cannabinoids in the extract may be 5% or more, for example, 5% to 9%, 5% to 8%, 5% to 7%, or 5% to 6%, based on the weight of the extract. The extract has no phase separation when concentrated, and may have high solubility.

In the method, the extract may be obtained by a method including incubating a reaction mixture including cannabinoids and the aprotonic solvent. The incubating may be performed at 20° C., 25° C., 30° C., or 35° C. to a reflux temperature of a single solvent or a mixed solvent used.

In the method, the aprotonic solvent may be ethyl acetate, acetone, 2-butanone, chloroform, dichloromethane, hexane, or a mixture thereof.

In the method, the *Cannabis* sp. plant may be leaves, flower buds, fruits, trichomes, flower bracts, stems, or any part including cannabinoid.

In the method, the content of CBDA and CBD in the extract may be 5% or more, for example, 5% to 9%, 5% to 8%, 5% to 7%, or 5% to 6%, based on the total weight of the extract.

Conversion of CBDA included in the *cannabis* plant or the extract thereof into CBD through decarboxylic acid reaction may be achieved by microwave irradiation.

In the method, an appropriate temperature of the microwave irradiation may be selected according to the solvent, the content of CBD in a final product, or a ratio of CBD to CBDA. The microwave irradiation may be carried out at 80° C. to 150° C., for example, 80° C. to 140° C., 80° C. to 130° C., 80° C. to 120° C., 80° C. to 110° C., 80° C. to 100° C., 80° C. to 90° C., 90° C. to 150° C., 90° C. to 140° C., 90° C. to 130° C., 90° C. to 120° C., 90° C. to 110° C., 90° C. to 100° C., 100° C. to 150° C., 100° C. to 140° C., 100° C. to 130° C., 100° C. to 120° C., 100° C. to 110° C., 110° C. to 150° C., 110° C. to 140° C., 110° C. to 130° C., 110° C. to 120° C., 120° C. to 150° C., 120° C. to 140° C., or 120° C. to 130° C.

In the method, the microwave irradiation may be carried out for a time sufficient to convert CBDA to CBD. The microwave irradiation time may vary depending on the temperature, a microwave output power, the solvent used, and use of the final product. The microwave irradiation time may be 5 min to 180 min, for example, 10 min to 180 min, 10 min to 150 min, 10 min to 100 min, 10 min to 90 min, 20 min to 180 min, 20 min to 150 min, 20 min to 100 min, 20 min to 90 min, 30 min to 180 min, 30 min to 150 min, 30 min to 100 min, or 30 min to 90 min.

In the method, the microwave irradiation may be carried out under pressure. The microwave irradiation may be carried out under a pressure of more than 1 atm to 100 atm, for example, 2 atm to 100 atm, 2 atm to 50 atm, 2 atm to 30 atm, 2 atm to 20 atm, or 2 atm to 15 atm.

In the microwave irradiation of the method, the microwave output power may be 50 W to 6 kW, for example, 100 W to 3 kW.

In the method, the microwave irradiation indicates a thermal reaction of heating the *cannabis* plant or the extract thereof by irradiating microwaves thereto. The microwave may be a microwave having a frequency of 300 MHz to 300 GHz, for example, 1000 MHz to 100 GHz, 1000 MHz to 50 GHz, 1000 MHz to 10 GHz, or 1000 MHz to 5 GHz.

In the method, the isolated cannabinoid may be CBD.

In the microwave irradiation of the method, the solvent may be an aprotonic solvent. The aprotonic solvent may be C3-C10 ester, C3-C10 ketone, or unsubstituted or halogenated C1-C6 hydrocarbon. The aprotonic solvent may be ethyl acetate, acetone, 2-butanone, chloroform, dichloromethane, hexane, or a mixture thereof.

The microwave irradiation may be carried out to convert 10% to 100%, for example, 25% to 100%, 30% to 100%, 50% to 100%, 80% to 100%, 90% to 100%, 95% to 100%, 97% to 100%, or 100% of the CBDA ingredient included in the *Cannabis* sp. plant or the extract thereof into the CBD ingredient.

In the method, the isolated cannabinoid may include 10% by weight to 100% by weight of CBD, based on the total weight of the isolate.

The method may include isolating cannabinoid from the microwave-irradiated reaction mixture. The isolating may be isolating CBD.

The isolating may include performing chromatography of the microwave-irradiated reaction mixture. The chromatography may be, for example, reverse-phase C18 column chromatography or reverse-phase semi-preparative high performance liquid chromatography. As a result, the reaction mixture may be a polar fraction of the solvent by silica gel, and a mixture with a high content of CBD or a single ingredient of CBD by isolation through preparative liquid chromatography may be obtained.

The isolation method by reverse-phase C18 column chromatography is an isolation method commonly used in a laboratory. Depending on the amount of a sample to be separated, a diameter of a glass column to be used and the amount of reverse-phase C18 to be used may vary. Generally, in the case of the glass column, a column having an internal diameter of 1 cm to 10 cm and a length of 10 cm to 100 cm, in which 50% to 70% of the height of the column is packed with reversed phase C18, may be generally used. A composition of an eluent to be used slightly varies depending on the amount of the sample and the silica gel column, for example, a mixed solvent having a volume ratio of methanol:water:ethyl acetate=1:1:0 to 1:0:0 to 0:0:1 may be sequentially used according to the mixing ratio.

The isolation conditions by reverse-phase semi-preparative HPLC may vary depending on the amount of the sample and the size of a column to be used. Generally, reverse-phase preparative HPLC (stationary phase: Luna C18(2) column, Phenomenex, particle size of 10 μm, length of 250 mm×10 mm) is prepared in a liquid chromatography (Shimadzu) instrument, and the sample dissolved in an initial eluent is injected, and then isolation may be performed while developing the eluent from acetonitrile:water=50:50 (v/v) to acetonitrile:water=100:0 (v/v) for 60 min to 90 min.

Another aspect provides an antiepileptic, neuroprotective, vasorelaxant, anti-cancer, anti-inflammatory, anti-diabetic, anti-bacterial, analgesic, anti-osteoporosis, immune-enhancing, or antiemetic pharmaceutical composition, the pharmaceutical composition including, as an active ingredient, the cannabinoid isolated by the above method. The cannabinoid may be CBD. The cannabinoid may be in the form of an extract, a fraction, or a single ingredient. The pharmaceutical composition may further include a pharmaceutically acceptable carrier or diluent.

The cannabinoid has improved CBD efficacy due to a significantly high content of CBD, as compared with a processed product resulting from simple heat-treatment.

CBD is known to have antiepileptic, neuroprotective, vasorelaxant, anti-cancer, anti-inflammatory, anti-diabetic, antibacterial, analgesic, anti-osteoporosis, immune-enhancing, or antiemetic effects. Therefore, these effects may be significantly increased by the microwave irradiation, as compared with a processed product resulting from simple heat-treatment.

Still another aspect provides a health functional food composition including, as an active ingredient, the cannabinoid isolated by the above method. The cannabinoid may be CBD. The cannabinoid may be in the form of an extract, a fraction, or a single ingredient. The food may be a functional food or a health functional food. The functional ingredient of the food is a safe food composition partially including the pharmaceutical ingredient, and may further include a carrier or diluent acceptable for use in foods.

Still another aspect provides a cosmetic composition including, as an active ingredient, the cannabinoid isolated by the above method. The cosmetics may be a general cosmetics or a functional cosmetics. CBD, known as a functional ingredient of cosmetics, may be a composition having an antioxidant or anti-inflammatory effect. The cosmetic composition may further include a carrier or diluent acceptable for use in cosmetics.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
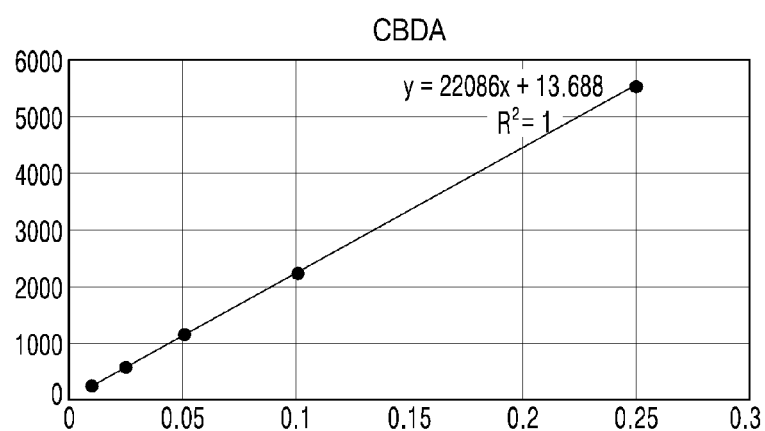
FIG. 1 shows a calibration curve constructed by analyzing CBDA according to concentrations.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in more detail with reference to exemplary embodiments. However, these exemplary embodiments are only for illustrating the present disclosure, and the scope of the present disclosure is not limited to these exemplary embodiments.

Comparative Example 1 and Examples 1 to 7:
Comparison of *Cannabis* Extracts According to Extraction Solvents

*Cannabis* used in the present Comparative Examples and Examples was deposited by JayHempKorea Ltd., located in Sangju city, Gyeongsangbuk-do, South Korea, through assignment/transfer approval processes under drug (*cannabis*) research permission (No. 1564) obtained from the Ministry of Food and Drug Safety and Seoul Regional Food and Drug Administration. *Cannabis* seed skins, *cannabis* leaves, *cannabis* stems, and *cannabis* roots were harvested in October, 2018, and used after being dried and finely cut. 20 mL of an extraction solvent was added to 1 g of finely cut and dried *cannabis* leaves having a relatively high content of cannabinoids among the parts of *cannabis* in 100 mL Erlenmeyer flask, and extracted using an ultrasonic processor (Sonics, VC505) at 40% power of the instrument for 1 hr, and then extracted at room temperature for 24 hr. The used extraction solvents were ethanol (Comparative Example 1), butanol (Example 1), ethyl acetate (Example 2), acetone (Example 3), 2-butanone (Example 4), chloroform (Example 5), dichloromethane (Example 6), and hexane (Example 7).

Example 8: Preparation of *Cannabis* Leaf Extract

In this Example, extracts were prepared in the same manner as in Example 2, and *cannabis* leaves harvested in October, 2018 were used after being dried and finely cut. 200 g of the finely cut and dried *cannabis* leaves and 2 L of ethyl acetate were put in a 5 L-beaker, and extracted using an ultrasonic processor at 40% power of the instrument for 1 hr, and then extracted at room temperature for 24 hr. These procedures were repeated twice. The liquid extract was concentrated by evaporation under reduced pressure to obtain 17.6 g of a dry extract including CBDA and CBD.

Examples 9 to 30: Microwave Processing of *Cannabis* Leaf Extract

The ethyl acetate extract obtained in Example 8 was subjected to microwave processing. In detail, 100 mg of the *cannabis* leaf extract was added to 1 mL of ethyl acetate in a 10-mL container of a microwave irradiator (model no. 908005) manufactured by CEM Company (USA), followed by sealing the container. Microwaves were irradiated at a power of 100 W and a frequency of 2450 MHz, at 80° C. for 10 min (Example 9), 20 min (Example 10), and 30 min (Example 11), at 90° C. for 10 min (Example 12), 20 min (Example 13), and 30 min (Example 14), at 100° C. for 10 min (Example 15), 20 min (Example 16), and 30 min (Example 17), at 110° C. for 10 min (Example 18), 20 min (Example 19), and 30 min (Example 20), at 120° C. for 10 min (Example 21), 20 min (Example 22), 30 min (Example 23), 40 min (Example 24), and 50 min (Example 25), at 130° C. for 5 min (Example 26), 10 min (Example 27), 20 min (Example 28), 30 min (Example 29), and 40 min (Example 30), respectively. The extracts were dried under reduced pressure to obtain microwave-irradiated process products, respectively. A pressure for the microwave irradiation was 1 atm to 15 atm. Contents thereof were analyzed according to an analysis method of Experimental Example 1.

Examples 31 to 38: Microwave Processing of *Cannabis*

The dried *cannabis* leaves were subjected to microwave processing using ethanol, butanol, ethyl acetate, acetone, 2-butanone, chloroform, dichloromethane, and hexane solvents. In detail, 1 g of *cannabis* leaves which were harvested in October, 2018 and dried and then finely cut was added to 7 mL of a solvent in a 40-mL container of a microwave irradiator (model no. 908005) manufactured by CEM Company (USA), followed by sealing the container. Processing was conducted at 300 W and a frequency of 2450 MHz for 30 min. The microwave processing temperature according to the used solvent was 130° C. for ethanol (Example 31), 130° C. for butanol (Example 32), 130° C. for ethyl acetate (Example 33), 90° C. for acetone (Example 34), 100° C. for 2-butanone (Example 35), 130° C. for chloroform (Example 36), 95° C. for dichloromethane (Example 37), and 130° C. for hexane (Example 38), respectively. A pressure for the microwave irradiation was 5 atm to 15 atm. Contents thereof were analyzed according to an analysis method of Experimental Example 1.

Examples 39 to 51: Microwave Processing of *Cannabis* Leaves

The dried *cannabis* leaves were subjected to microwave processing using ethyl acetate. In detail, 1 g of *cannabis* leaves which were dried and then finely cut was added to 7 mL of ethyl acetate in a 40-mL container of a microwave irradiator (model no. 908005) manufactured by CEM Company (USA), followed by sealing the container. Microwaves were irradiated at a power of 300 W and a frequency of 2450 MHz, at 120° C. for 30 min (Example 39), 60 min (Example 40), 90 min (Example 41), 120 min (Example 42), and 150 min (Example 43), at 130° C. for 10 min (Example 44), 20 min (Example 45), 30 min (Example 46), 40 min (Example 47), 50 min (Example 48), at 140° C. for 10 min (Example 49), 20 min (Example 50), and 30 min (Example 51), respectively. A pressure for the microwave irradiation was 5 atm to 15 atm. Contents thereof were analyzed according to an analysis method of Experimental Example 1.

Experimental Example 1: Analysis of Cannabinoids in Extracts and Microwave-Processed Products (1) Experimental Method Based on values of CBDA and CBD calibration curves, cannabinoids in the *cannabis* leaf extracts and the processed extracts obtained in Comparative Examples and Examples were analyzed, and repeated in triplicate to confirm reproducibility. As for CBDA and CBD single ingredients used in the experiments, purity of 97.1% (CBDA) and purity of 96.3% (CBD) directly isolated from the *cannabis* leaf raw material were used. According to the general calibration curve analysis method, CBDA and CBD were prepared at 10 ppm, 25 ppm, 50 ppm, 100 ppm, and 250 ppm, respectively, and calibration curves were constructed. An elution solvent A and an elution solvent B used in ultra-performance liquid chromatography (UPLC) were water and acetonitrile, respectively, and each was pumped using two pumps. 3 µl of the standard aqueous solution was injected into a reverse-phase column for analysis (Phenomenex Luna Omega 1.6µ Polar C18, 150 mm×2.1 mm) using a syringe, and an elution solvent consisting of 70% by volume of A and 30% by volume of B was applied at a flow rate of 0.3 mL/min. Thereafter, % volume of the elution solvent B were gradually changed to 100% (20 min), 100% (23 min), and 30% (26 min). After the above procedures, each ingredient isolated from the column was analyzed by UV spectrum.

(2) Experimental Results

As a result of the experiments, each ingredient isolated from the column was analyzed by UPLC analysis of the *cannabis* leaf extracts, and peaks of FIGS. 3 to 14 were obtained by the analysis results of UPLC chromatograms.

FIG. 1 shows a calibration curve constructed by analyzing CBDA according to concentrations.

Figure 2:
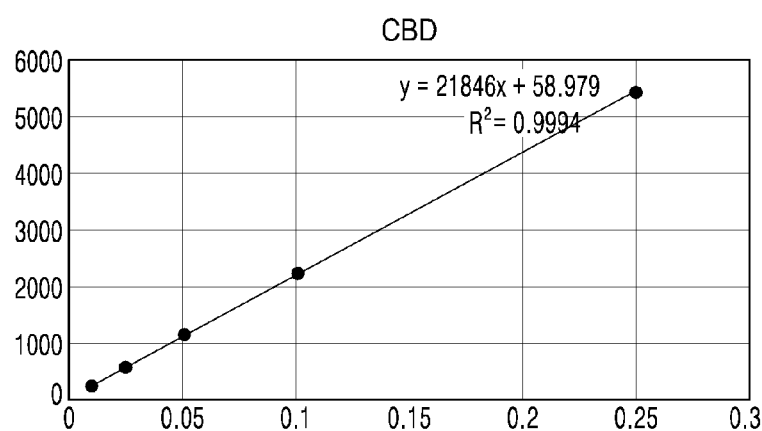
FIG. 2 shows a calibration curve constructed by analyzing CBD according to concentrations.

FIG. 2 shows a calibration curve constructed by analyzing CBD according to concentrations.

Figure 3:
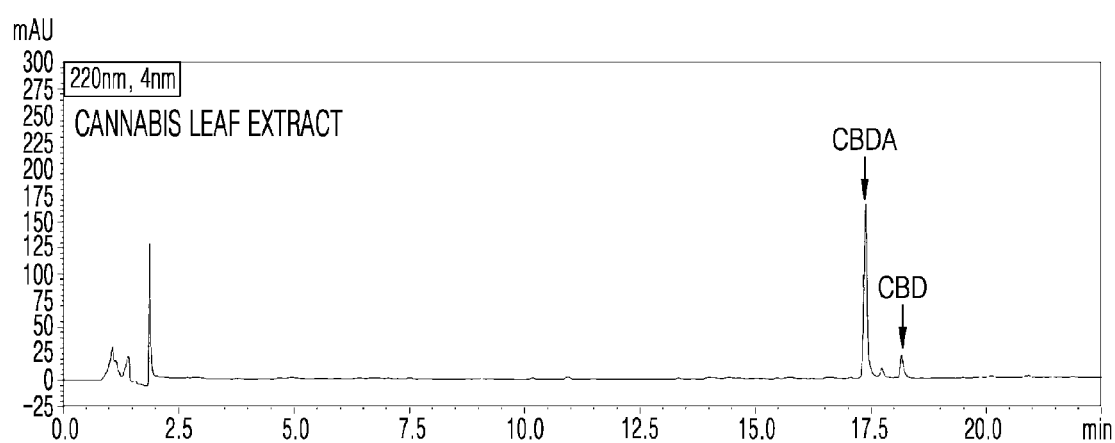
FIG. 3 shows a UPLC chromatogram of analyzing cannabinoid ingredients in an extract of a raw material *cannabis* leaf, hereinbelow, the "extract of the raw material *cannabis* leaf" represents an extract obtained in Example 8 by extraction with an ethyl acetate solvent.

FIG. 3 shows a UPLC chromatogram of analyzing cannabinoid ingredients in an extract of a raw material *cannabis* leaf. Hereinbelow, the "extract of the raw material *cannabis* leaf" represents an extract obtained in Example 1 by extraction with an ethyl acetate solvent.

Figure 4:
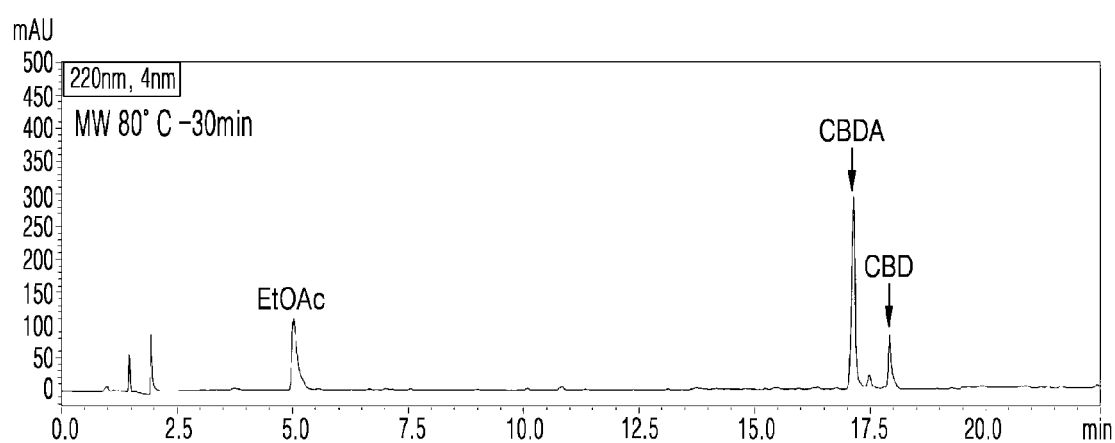
FIG. 4 shows a UPLC chromatogram of analyzing cannabinoid ingredients in a microwave-irradiated processed product obtained by treating the extract of *cannabis* leaves with microwaves at 80° C. and 100 W for 30 min.

FIG. 4 shows a UPLC chromatogram of analyzing cannabinoid ingredients in a microwave-irradiated processed product obtained by treating the extract of *cannabis* leaves with microwaves at 80° C. and 100 W for 30 min.

Figure 5:
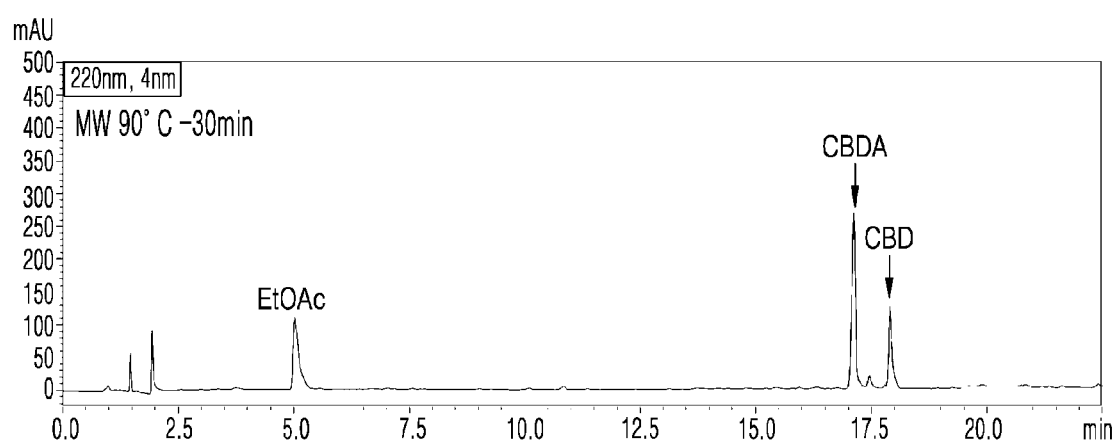
FIG. 5 shows a UPLC chromatogram of analyzing cannabinoid ingredients in a microwave-irradiated processed product obtained by treating the extract of *cannabis* leaves with microwaves at 90° C. and 100 W for 30 min.

FIG. 5 shows a UPLC chromatogram of analyzing cannabinoid ingredients in a microwave-irradiated processed product obtained by treating the extract of *cannabis* leaves with microwaves at 90° C. and 100 W for 30 min.

Figure 6:
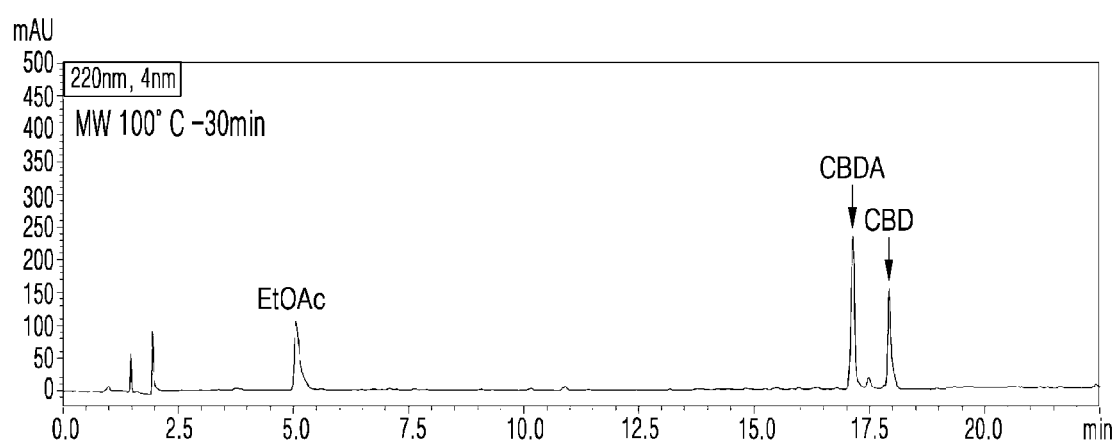
FIG. 6 shows a UPLC chromatogram of analyzing cannabinoid ingredients in a microwave-irradiated processed product obtained by treating the extract of *cannabis* leaves with microwaves at 100° C. and 100 W for 30 min.

FIG. 6 shows a UPLC chromatogram of analyzing cannabinoid ingredients in a microwave-irradiated processed product obtained by treating the extract of *cannabis* leaves with microwaves at 100° C. and 100 W for 30 min.

Figure 7:
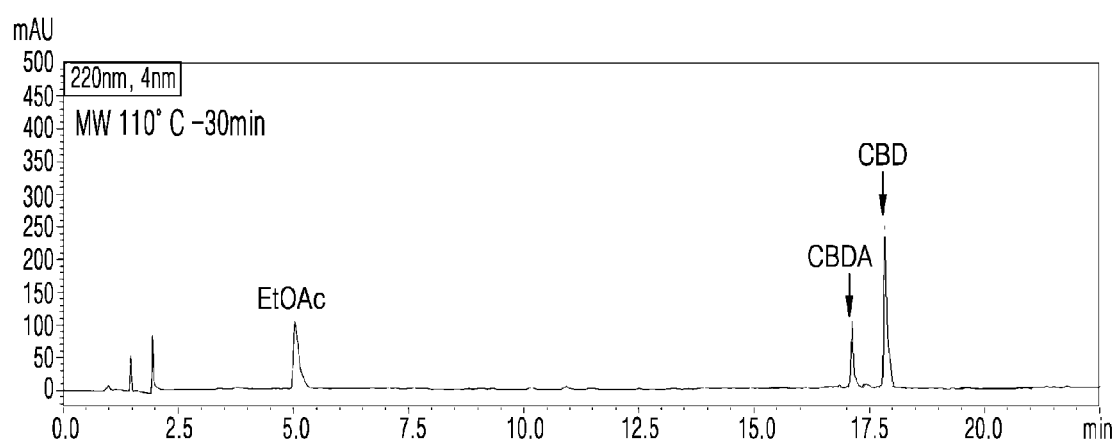
FIG. 7 shows a UPLC chromatogram of analyzing cannabinoid ingredients in a microwave-irradiated processed product obtained by treating the extract of *cannabis* leaves with microwaves at 110° C. and 100 W for 30 min.

FIG. 7 shows a UPLC chromatogram of analyzing cannabinoid ingredients in a microwave-irradiated processed product obtained by treating the extract of *cannabis* leaves with microwaves at 110° C. and 100 W for 30 min.

Figure 8:
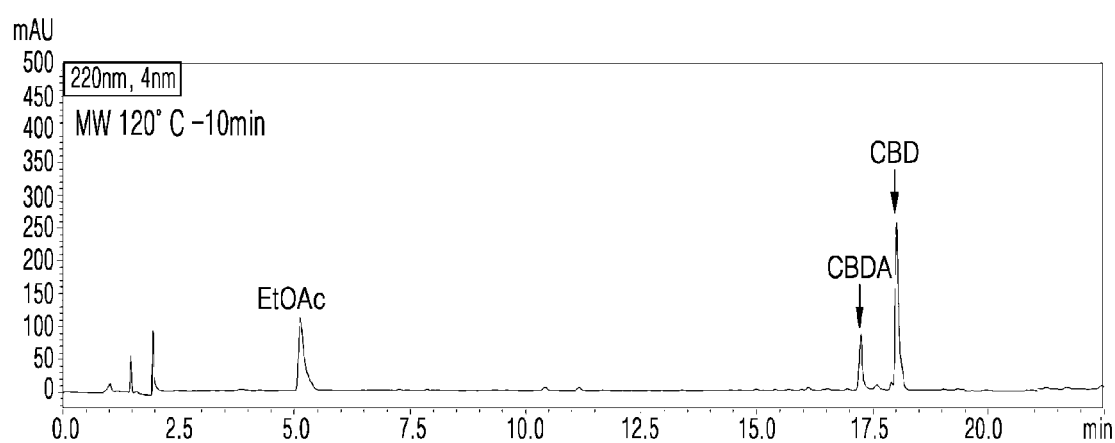
FIG. 8 shows a UPLC chromatogram of analyzing cannabinoid ingredients in a microwave-irradiated processed product obtained by treating the extract of *cannabis* leaves with microwaves at 120° C. and 100 W for 10 min.

FIG. 8 shows a UPLC chromatogram of analyzing cannabinoid ingredients in a microwave-irradiated processed product obtained by treating the extract of *cannabis* leaves with microwaves at 120° C. and 100 W for 10 min.

Figure 9:
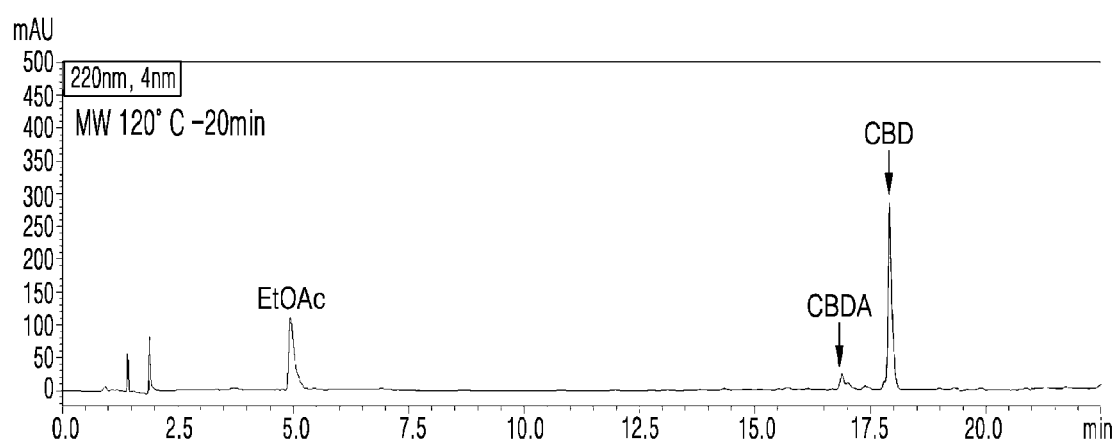
FIG. 9 shows a UPLC chromatogram of analyzing cannabinoid ingredients in a microwave-irradiated processed product obtained by treating the extract of *cannabis* leaves with microwaves at 120° C. and 100 W for 20 min.

FIG. 9 shows a UPLC chromatogram of analyzing cannabinoid ingredients in a microwave-irradiated processed product obtained by treating the extract of *cannabis* leaves with microwaves at 120° C. and 100 W for 20 min.

Figure 10:
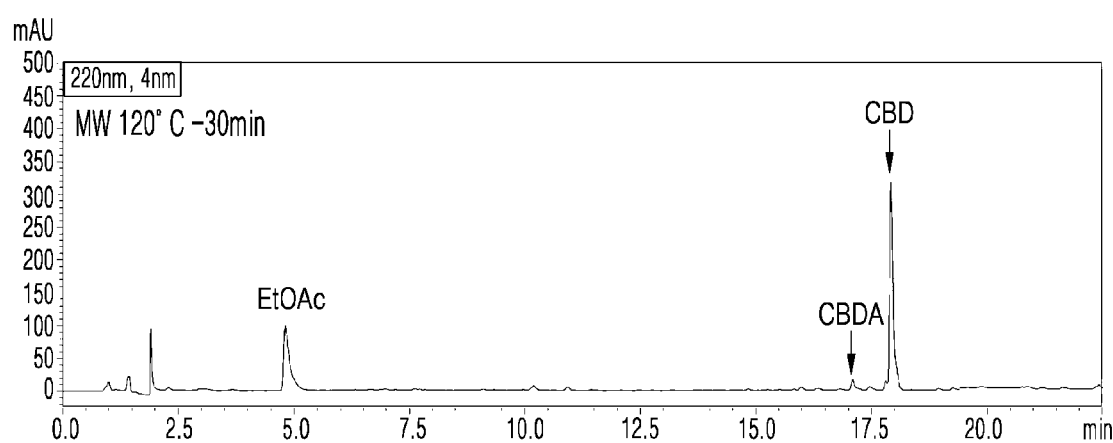
FIG. 10 shows a UPLC chromatogram of analyzing cannabinoid ingredients in a microwave-irradiated processed product obtained by treating the extract of *cannabis* leaves with microwaves at 120° C. and 100 W for 30 min.

FIG. 10 shows a UPLC chromatogram of analyzing cannabinoid ingredients in a microwave-irradiated processed product obtained by treating the extract of *cannabis* leaves with microwaves at 120° C. and 100 W for 30 min.

Figure 11:
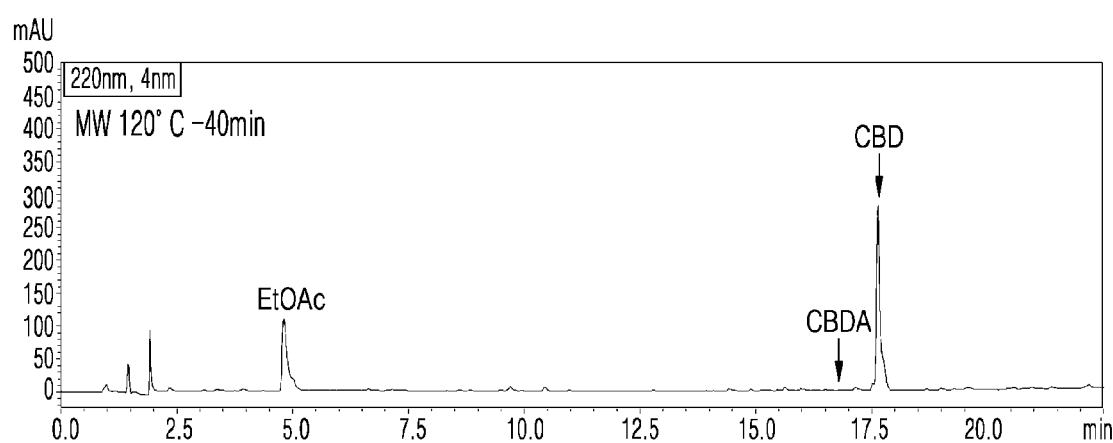
FIG. 11 shows a UPLC chromatogram of analyzing cannabinoid ingredients in a microwave-irradiated processed product obtained by treating the extract of *cannabis* leaves with microwaves at 120° C. and 100 W for 40 min.

FIG. 11 shows a UPLC chromatogram of analyzing cannabinoid ingredients in a microwave-irradiated processed product obtained by treating the extract of *cannabis* leaves with microwaves at 120° C. and 100 W for 40 min.

Figure 12:
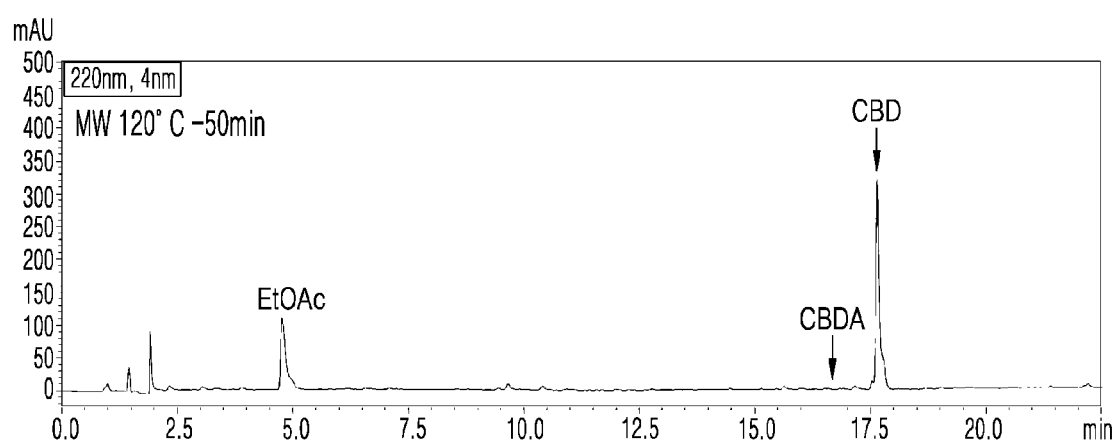
FIG. 12 shows a UPLC chromatogram of analyzing cannabinoid ingredients in a microwave-irradiated processed product obtained by treating the extract of *cannabis* leaves with microwaves at 120° C. and 100 W for 50 min.

FIG. 12 shows a UPLC chromatogram of analyzing cannabinoid ingredients in a microwave-irradiated processed product obtained by treating the extract of *cannabis* leaves with microwaves at 120° C. and 100 W for 50 min.

Figure 13:
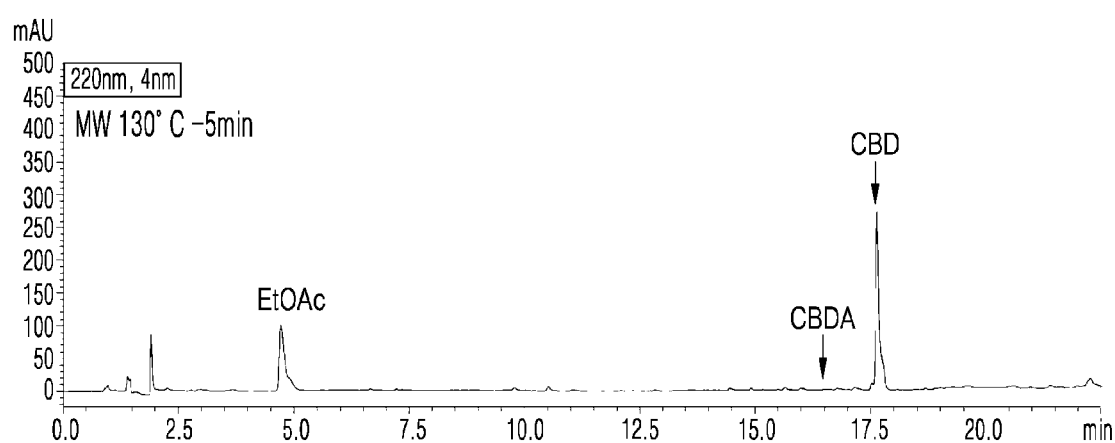
FIG. 13 shows a UPLC chromatogram of analyzing cannabinoid ingredients in a microwave-irradiated processed product obtained by treating the extract of *cannabis* leaves with microwaves at 130° C. and 100 W for 5 min.

FIG. 13 shows a UPLC chromatogram of analyzing cannabinoid ingredients in a microwave-irradiated processed product obtained by treating the extract of *cannabis* leaves with microwaves at 130° C. and 100 W for 5 min.

Figure 14:
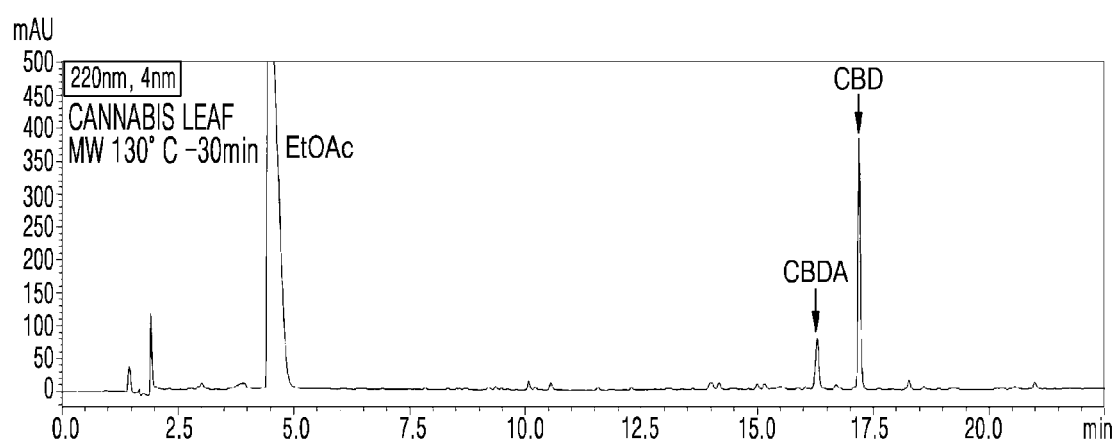
FIG. 14 shows a UPLC chromatogram of analyzing cannabinoid ingredients in a microwave-irradiated processed product obtained by treating the *cannabis* leaves with microwaves at 130° C. and 100 W for 30 min.

FIG. 14 shows a UPLC chromatogram of analyzing cannabinoid ingredients in a microwave-irradiated processed product obtained by treating the *cannabis* leaves with microwaves at 130° C. and 100 W for 30 min.

Figure 15:
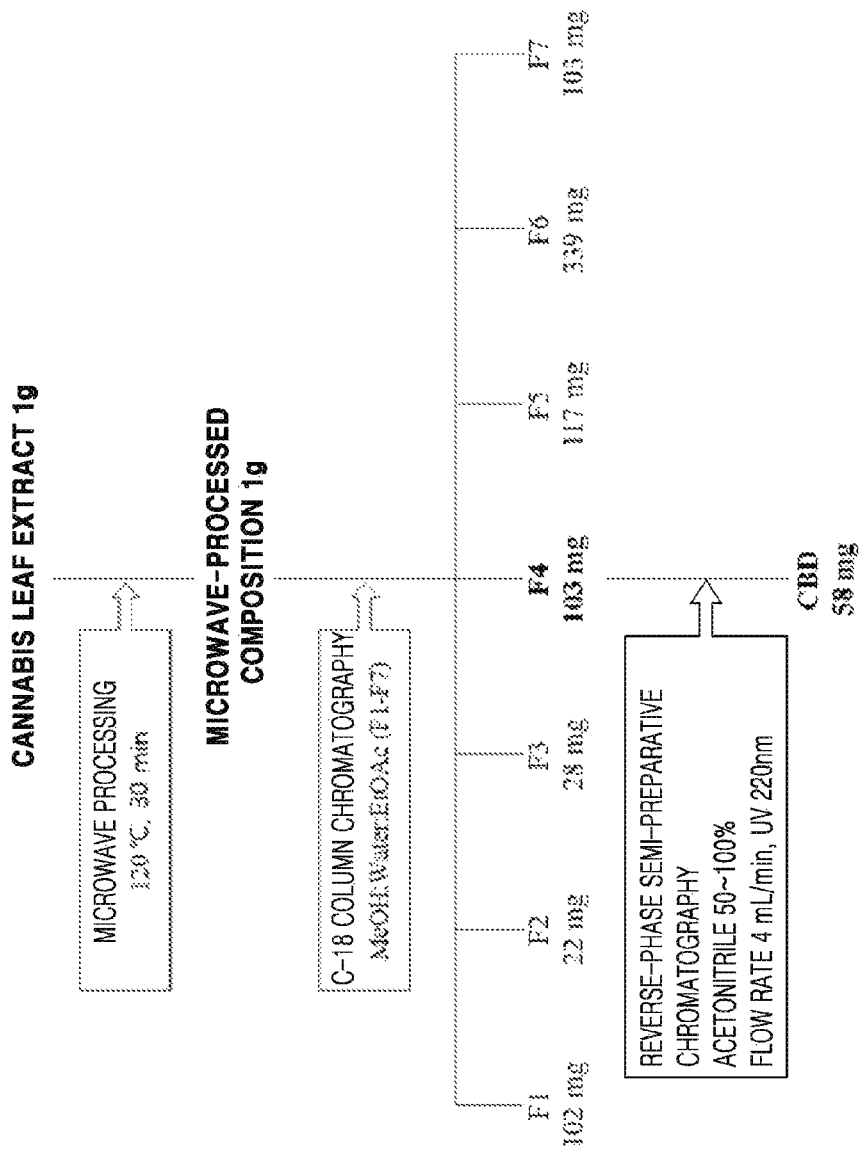
FIG. 15 shows a diagram of a process of isolating CBD from a processed product of Example 23.

FIG. 15 shows a diagram of a process of isolating CBD from the processed product of Example 23.

Figure 16A:
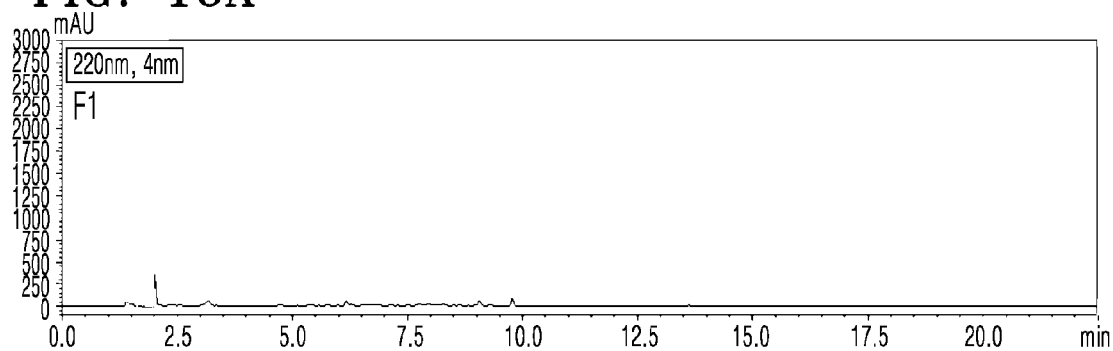
FIGS. 16A and 16B show a UPLC chromatogram of analyzing cannabinoid ingredients in a fraction of the processed product of Example 23.
Figure 16A:
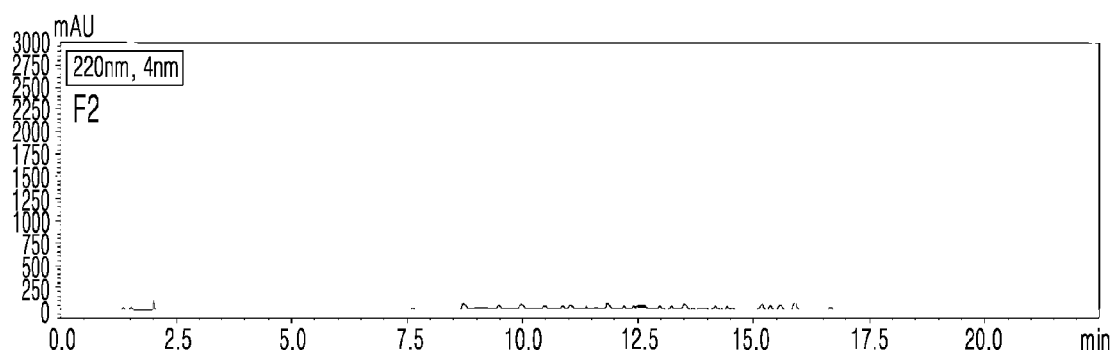
Figure 16A:
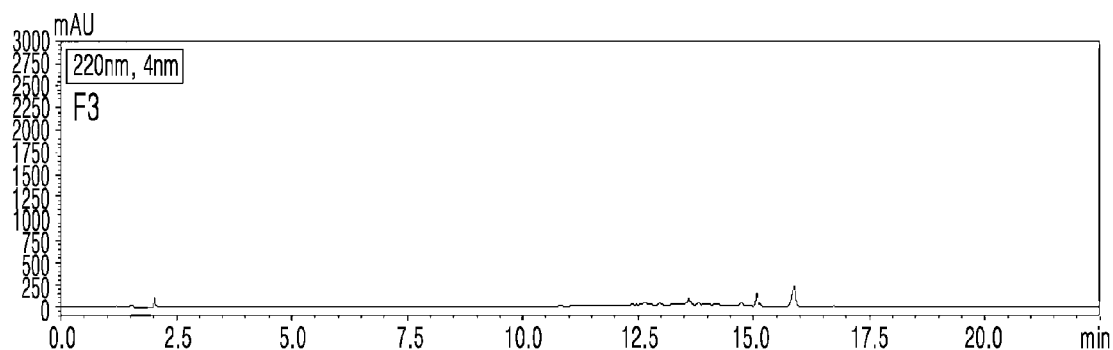
Figure 16A:
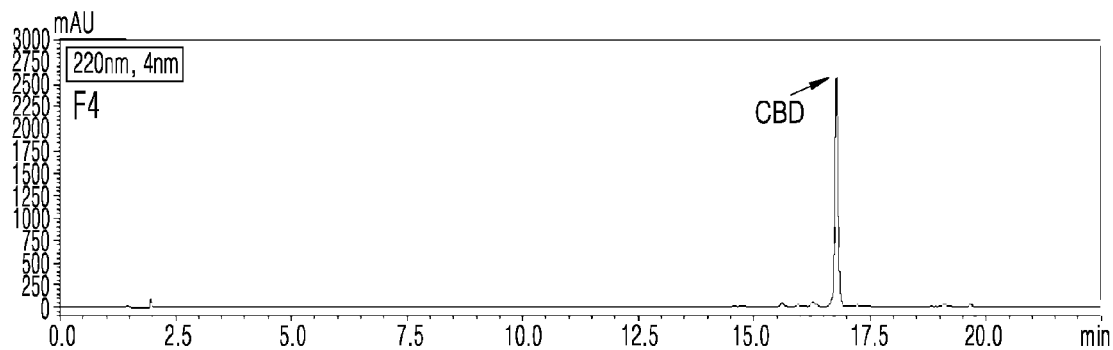
Figure 16B:
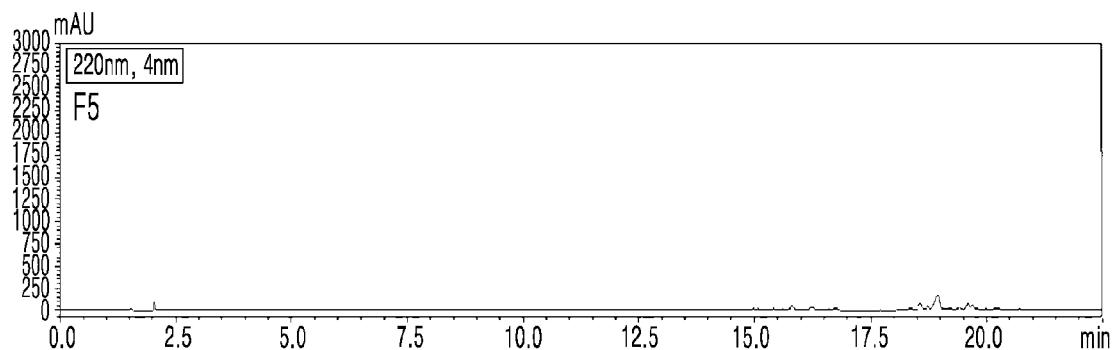
Figure 16B:
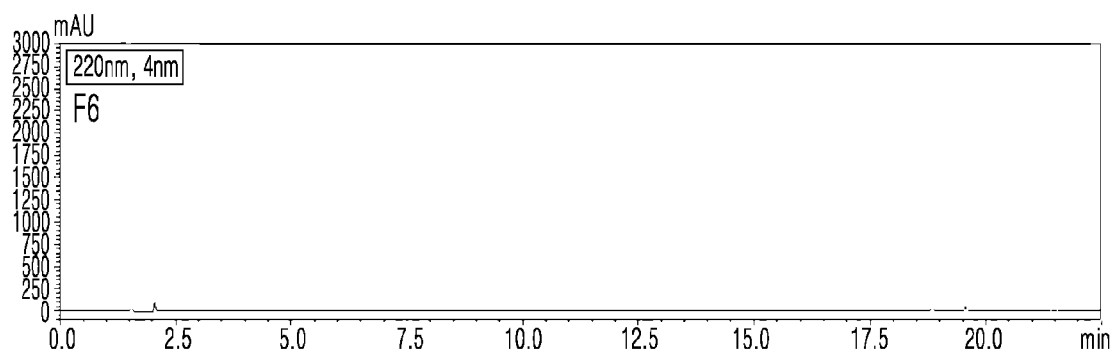
Figure 16B:
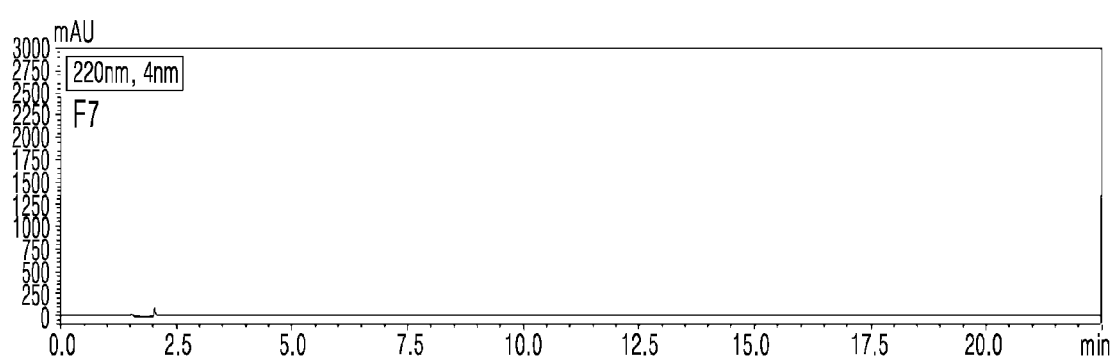

FIGS. 16A and 16B show a UPLC chromatogram of analyzing cannabinoid ingredients in a fraction of the processed product of Example 23.

Further, the contents of CBDA and CBD according to the extraction solvents are summarized in Table 1.

TABLE 1

| Item | Amount of extract | CBDA | CBD | CBDA + CBD | CBDA + CBD content % in extract |
|---|---|---|---|---|---|
| Comparative Example 1 | 166.3 mg | 5.62 mg | 0.03 mg | 5.65 mg | 3.40% |
| Example 1 | 84.3 mg | 5.96 mg | 0.23 mg | 6.19 mg | 7.34% |
| Example 2 | 90.0 mg | 7.70 mg | 0.16 mg | 7.86 mg | 8.73% |
| Example 3 | 86.7 mg | 6.66 mg | 0.13 mg | 6.79 mg | 7.83% |
| Example 4 | 115.7 mg | 5.87 mg | 0.05 mg | 5.92 mg | 5.12% |
| Example 5 | 112.8 mg | 6.09 mg | 0.13 mg | 6.22 mg | 5.51% |
| Example 6 | 83.0 mg | 6.16 mg | 0.26 mg | 6.42 mg | 7.74% |
| Example 7 | 70.0 mg | 5.17 mg | 0.27 mg | 5.44 mg | 7.77% |

In Table 1, the amount of the extract and the contents of CBDA and CBD are shown according to each solvent, in which 1 g of *cannabis* leaves was extracted using 8 kinds of extraction solvents; ethanol (Comparative Example 1), butanol (Example 1), ethyl acetate (Example 2), acetone (Example 3), 2-butanone (Example 4), chloroform (Example 5), dichloromethane (Example 6), and hexane (Example 7). 166.3 mg of the largest amount of the *cannabis* leaf extract was obtained by ethanol extraction, followed by 2-butanone (115.7 mg), chloroform (112.8 mg), ethyl acetate (90.0 mg), acetone (86.7 mg), butanol (84.3 mg), dichloromethane (83.0 mg), and hexane (70.0 mg) extractions. However, the highest total amount (7.86 mg) of CBDA and CBD which are active ingredients of *cannabis* was obtained by ethyl acetate extraction, followed by acetone (6.79 mg), dichloromethane (6.42 mg), chloroform (6.22 mg), butanol (6.19 mg), 2-butanone (5.92 mg), ethanol (5.65 mg), and hexane (5.44 mg) extractions. As a result, when ethanol was used as the extraction solvent, the largest amount of the extract was obtained, but it was found that ethanol is not suitable as a solvent to obtain CBDA and CBD which are pharmaceutical ingredients of *cannabis*. In contrast, when ethyl acetate was used as the extraction solvent, the amount of the extract was about 54% of the amount of the ethanol extract, but 39% or more increase was observed in the content of CBDA+CBD. Although butanol is alcohol, it is an oil-soluble alcohol. Thus, it was confirmed that butanol is an extraction solvent to obtain a relatively high content of CBDA and CBD. Accordingly, it was confirmed that ethyl acetate is the best extraction solvent for extracting cannabinoids from *cannabis* leaves.

Further, Table 2 summarizes the results of calculating the contents of CBDA and CBD in UPLC chromatograms obtained after microwave processing of the *cannabis* leaf extracts.

TABLE 2

| Item | Temperature (° C.)-Time (min) | CBDA | CBD | CBDA + CBD | CBD production yield * | CBD content % = {CBD/(CBDA + CBD)} × 100 |
|---|---|---|---|---|---|---|
| Example 8 | - | 68.2 mg | 8.9 mg | 77.1 mg | 13.0% | 11.5% |
| Example 9 | 80-10 | 63.4 mg | 13.3 mg | 76.7 mg | 19.4% | 17.3% |
| Example 10 | 80-20 | 59.9 mg | 15.5 mg | 75.4 mg | 22.6% | 20.6% |
| Example 11 | 80-30 | 58.0 mg | 16.7 mg | 74.7 mg | 24.3% | 22.4% |
| Example 12 | 90-10 | 60.2 mg | 16.2 mg | 76.4 mg | 23.6% | 21.2% |
| Example 13 | 90-20 | 52.9 mg | 20.9 mg | 73.8 mg | 30.4% | 28.3% |
| Example 14 | 90-30 | 49.1 mg | 24.5 mg | 73.6 mg | 35.7% | 33.3% |
| Example 15 | 100-10 | 57.8 mg | 18.6 mg | 76.4 mg | 27.1% | 24.3% |
| Example 16 | 100-20 | 47.8 mg | 25.7 mg | 73.5 mg | 37.4% | 35.0% |
| Example 17 | 100-30 | 37.5 mg | 31.6 mg | 69.1 mg | 46.0% | 45.7% |
| Example 18 | 110-10 | 54.2 mg | 19.2 mg | 73.4 mg | 27.9% | 26.2% |
| Example 19 | 110-20 | 43.6 mg | 26.9 mg | 70.5 mg | 39.1% | 38.2% |

TABLE 2-continued

| Item | Temperature (° C.)-Time (min) | CBDA | CBD | CBDA + CBD | CBD production yield * | CBD content % = {CBD/(CBDA + CBD)} × 100 |
|---|---|---|---|---|---|---|
| Example 20 | 110-30 | 34.6 mg | 34.1 mg | 68.7 mg | 49.6% | 49.6% |
| Example 21 | 120-10 | 15.3 mg | 50.4 mg | 65.8 mg | 73.3% | 76.6% |
| Example 22 | 120-20 | 4.5 mg | 61.3 mg | 65.8 mg | 89.2% | 93.2% |
| Example 23 | 120-30 | 2.6 mg | 62.0 mg | 64.6 mg | 90.3% | 96.0% |
| Example 24 | 120-40 | 0.6 mg | 61.4 mg | 62.0 mg | 89.4% | 99.0% |
| Example 25 | 120-50 | 0.5 mg | 60.9 mg | 61.3 mg | 88.6% | 99.3% |
| Example 26 | 130-05 | 1.7 mg | 56.8 mg | 58.6 mg | 82.7% | 96.9% |
| Example 27 | 130-10 | 0.5 mg | 55.0 mg | 55.5 mg | 80.0% | 99.1% |
| Example 28 | 130-20 | 0.5 mg | 52.6 mg | 53.0 mg | 76.5% | 99.2% |
| Example 29 | 130-30 | 0.1 mg | 48.2 mg | 48.3 mg | 70.1% | 99.8% |
| Example 30 | 130-40 | N.D | 45.8 mg | 45.8 mg | 66.6% | 100.0% |

* CBD production yield = (CBD (mg) produced in each Example/68.7 mg (amount of CBD produced in Example 8, regarded as 100%) × 100

Table 2 shows CBDA and CBD contents expressed in mg per 1 g of the extract, after dissolving the *cannabis* leaf extract of Example 8 in ethyl acetate and irradiating microwaves thereto. The initial *cannabis* leaf extract (Example 8) was found to include 68.2 mg of CBDA and 8.9 mg of CBD, indicating that CBDA is 88.5%. According to the temperature and time of the microwave irradiation, decarboxylic acid reaction occurred to convert CBDA into CBD, and as a result, the content of CBD in the processed product was increased. The experiments were carried out at a microwave processing temperature from 80° C. to 130° C. with 10° C. intervals, and measurement was carried out from 10 min to 50 min to examine the effect of time on temperature. That is, as the processing temperature and time increased, the conversion to CBD tended to increase. However, the actual production yield of CBD tended to decrease at 120° C. after 30 min. 100% of CBDA was completely converted to CBD at 130° C. after 40 min, but the actual production yield of CBD was 67%.

Further, Table 3 summarizes the results of calculating the contents of CBDA and CBD in UPLC chromatograms obtained after microwave processing of the *cannabis* leaf extracts obtained by directly using various extraction solvents.

TABLE 3

| Item | Temperature (° C.) | CBDA | CBD | CBDA + CBD | CBD content % = {CBD/(CBDA + CBD)}* 100 |
|---|---|---|---|---|---|
| Example 31 | 130 | 0.26 mg | 4.35 mg | 4.61 mg | 94.4% |
| Example 32 | 130 | 0.37 mg | 5.45 mg | 5.82 mg | 93.6% |
| Example 33 | 130 | 0.23 mg | 5.89 mg | 6.12 mg | 96.2% |
| Example 34 | 90 | 4.01 mg | 2.12 mg | 6.13 mg | 34.6% |

TABLE 3-continued

| Item | Temperature (° C.) | CBDA | CBD | CBDA + CBD | CBD content % = {CBD/(CBDA + CBD)}* 100 |
|---|---|---|---|---|---|
| Example 35 | 100 | 3.02 mg | 2.74 mg | 5.76 mg | 47.6% |
| Example 36 | 130 | 0.45 mg | 4.42 mg | 4.87 mg | 90.8% |
| Example 37 | 95 | 2.55 mg | 1.96 mg | 4.51 mg | 43.5% |
| Example 38 | 130 | 0.24 mg | 4.95 mg | 5.19 mg | 95.4% |

Table 3 shows the CBDA and CBD contents in the extracts resulting from direct microwave processing of *cannabis* leaves in each of 8 kinds of extraction solvents, the CBDA and CBD contents expressed in mg per 1 g of the *cannabis* leaves. The microwave processing was carried out under the same conditions of a processing temperature of 130° C., a processing time of 30 min, and 300 W. However, depending on the properties of the solvents of ethanol, butanol, ethyl acetate, chloroform, and hexane, the microwave processing may be carried out at a processing temperature of 130° C., but acetone, 2-butanone, and dichloromethane were tested only at a maximum temperature of 90° C., 100° C., and 95° C., respectively. As a result of microwave processing according to the solvents, it was finally confirmed that CBDA was converted to CBD by decarboxylic acid reaction, as in the processing of the above-described *cannabis* leaf extract. In addition, when the processing was carried out using ethyl acetate as the extraction solvent, the conversion to CBD was the highest, in which the amount thereof was 5.89 mg.

Further, Table 4 summarizes the results of calculating the contents of CBDA and CBD in UPLC chromatograms of the processed products according to microwave irradiation temperature and time by directly extracting *cannabis* leaves using the ethyl acetate solvent.

TABLE 4

| Item | Temperature (° C.)-Time (min) | CBDA | CBD | CBDA + CBD | CBD production yield | CBD content % = {CBD/(CBDA + CBD)}* 100 |
|---|---|---|---|---|---|---|
| Comparative Example 1 | — | 7.70 mg | 0.16 mg | 7.86 mg | 2.3% | 11.5% |
| Example 39 | 120-30 | 3.16 mg | 3.20 mg | 6.36 mg | 46.3% | 50.3% |
| Example 40 | 120-60 | 1.45 mg | 4.84 mg | 6.29 mg | 70.0% | 76.9% |
| Example 41 | 120-90 | 0.81 mg | 5.52 mg | 6.33 mg | 79.8% | 87.2% |

TABLE 4-continued

| Item | Temperature (° C.)-Time (min) | CBDA | CBD | CBDA + CBD | CBD production yield | CBD content % = {CBD/(CBDA + CBD)}* 100 |
|---|---|---|---|---|---|---|
| Example 42 | 120-120 | 0.40 mg | 5.72 mg | 6.12 mg | 82.7% | 93.5% |
| Example 43 | 120-150 | 0.20 mg | 5.59 mg | 5.79 mg | 80.9% | 96.5% |
| Example 44 | 130-10 | 2.17 mg | 4.18 mg | 6.35 mg | 60.5% | 65.8% |
| Example 45 | 130-20 | 1.21 mg | 4.92 mg | 6.13 mg | 71.2% | 80.3% |
| Example 46 | 130-30 | 0.23 mg | 5.89 mg | 6.12 mg | 85.2% | 96.2% |
| Example 47 | 130-40 | 0.21 mg | 5.52 mg | 5.73 mg | 79.8% | 96.3% |
| Example 48 | 130-50 | 0.12 mg | 5.31 mg | 5.43 mg | 76.8% | 97.8% |
| Example 49 | 140-10 | 0.52 mg | 5.64 mg | 6.16 mg | 81.6% | 91.6% |
| Example 50 | 140-20 | 0.08 mg | 5.81 mg | 5.89 mg | 84.0% | 98.6% |
| Example 51 | 140-30 | 0.07 mg | 5.46 mg | 5.53 mg | 79.0% | 98.7% |

Table 4 shows CBDA and CBD contents in the extracts resulting from microwave processing of *cannabis* leaves in the ethyl acetate solvent, the BDA and CBD contents expressed in mg per 1 g of the *cannabis* leaves. As a result of microwave processing of *cannabis* leaves, it was confirmed that CBDA was converted to CBD by decarboxylic acid reaction, as in the processing of the *cannabis* extract. In addition, as the temperature and processing time increased, the conversion to CBD was increased. When processed at 130° C. for 30 min, the maximum production yield of CBD was observed, and the CBD content was up to 85%.

As a result of the experiments, when microwaves were irradiated to the *cannabis* leaf extracts and *cannabis* leaves in various organic solvents in addition to ethanol, CBDA which is the main ingredient of the raw material *cannabis* leaf were more efficiently converted to CBD having excellent pharmaceutical efficacy, as demonstrated in existing literatures, academic researches, and patents.

For example, microwave-irradiated processed products having the CBD content of 20% to 100% with respect to the weight of the main cannabinoid ingredients of *cannabis* leaves were obtained.

Experimental Example 2: Isolation of Cannabinoids from Microwave-Processed Product of *Cannabis* Leaves (1) Experimental Method The microwave-processed product of *cannabis* leaves, which was obtained in Example 23, was applied to reverse-phase column chromatography to separate seven fractions, including a fraction having a high concentration of CBD.

1 g of the processed product of Example 23 was adsorbed onto 2 g of C18 (Nacalai tesque, Cosmosil C18), and then a glass column having an internal diameter of 2.8 cm was packed with C18 up to 10.0 cm in height, and a mixed solvent of methanol and water, and ethyl acetate were applied thereto. The eluted solvents were 50%, 60%, 70%, 80%, 90%, and 100% methanol and 100% ethyl acetate, and thus a total of seven fractions of F1 to F7 were obtained.

The seven fractions thus separated were analyzed in the same manner as in Experimental Example 1.

CBD was analyzed in the F4 fraction to attempt its isolation. Reverse-phase semi-preparative chromatography (stationary phase: Luna C18(2) column, Phenomenex, particle size of 10 μm, length of 250 mm×10 mm) was used to carry out isolation while developing an eluent from initial acetonitrile:water=50:50 (v/v) to acetonitrile:water=100:0 (v/v) for 60 min to 90 min at a flow rate of 4 mL/min, and one major peak at UV 220 nm was obtained.

(2) Experimental Results

As a result of the experiment, Example 23 was separated into seven fractions by reverse-phase C18 column chromatography. The fractions were 102 mg (fraction F1), 22 mg (fraction F2), 28 mg (fraction F3), 103 mg (fraction F4), 117 mg (fraction F5), 339 mg (fraction F6), and 103 mg (fraction F7), respectively. CBD was not observed in the fractions F1 to F3 and F5 to F7, whereas a large amount of CBD was observed in the fraction F4, which was then separated by reverse-phase semi-preparative chromatography. As a result, about 58 mg of CBD was obtained.

In conclusion, when CBD was isolated from the microwave-processed product of the *cannabis* leaf extract by reverse-phase C18 column chromatography and reverse-phase semi-preparative chromatography, 58 mg of CBD with purity of 99.2% was prepared from 1 g of *cannabis* leaf extract through decarboxylic acid reaction of CBDA by microwave irradiation.

According to the present disclosure, cannabinoids may be effectively extracted from a *cannabis* extract by using an aprotonic solvent, and in particular, the contents of CBDA and CBD in the extract may be increased.

According to the present disclosure, CBDA in the extract may be converted to CBD by microwave irradiation, and when an ethyl acetate extract having a high content of cannabinoids is irradiated with microwaves in a sealed reactor, 20 to 100% of CBD may be efficiently produced from CBDA by decarboxylic acid reaction.

According to the present disclosure, a fraction having a high content of CBD may be prepared by fractionation of a microwave-irradiated *cannabis* plant or an extract thereof through reverse-phase C18 column chromatography.

According to the present disclosure, a single ingredient of CBD may be prepared through reverse-phase semi-preparative high performance liquid chromatography of the fraction having a high content of CBD.

A pharmaceutical composition including the *cannabis* plant extract, the microwave-processed product, the fraction, or the single ingredient of CBD according to the present disclosure may be used in drugs and quasi-drugs for anti-epilepsy, neuroprotection, vasorelaxation, anti-cancer, anti-inflammation, anti-diabetes, anti-bacteria, analgesia, anti-osteoporosis, immune enhancement, or antiemetic action.

A food composition including the *cannabis* extract, the microwave-processed product, the fraction, or the single ingredient of CBD according to the present disclosure may be used as a food, in particular, as a functional food.

A cosmetic composition including the *cannabis* extract, the microwave-processed product, the fraction, or the single ingredient of CBD according to the present disclosure may be used in a general cosmetics or functional cosmetics with antioxidant or anti-inflammatory functions.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of isolating cannabidiol from *cannabis*, consisting essentially of:
    a) subjecting a reaction mixture consisting essentially of *cannabis* and ethyl acetate in an airtight container to microwaves to yield a microwave irradiated reaction mixture; and
    b) isolating cannabidiol from the microwave-irradiated reaction mixture, wherein the microwaves are carried out at 50 W to 6 kW, a frequency of 300 MHz to 300 GHz, 80° C. to 150° C. and at a pressure of 2 atm to 100 atm for 5 minutes to 180 minutes.

* * * * *